(12) United States Patent
Moses-Heller

(10) Patent No.: US 11,986,554 B2
(45) Date of Patent: *May 21, 2024

(54) ORALLY DISINTEGRATING COMPOSITIONS

(71) Applicant: DEXCEL PHARMA TECHNOLOGIES LTD., Jerusalem (IL)

(72) Inventor: Sheera Moses-Heller, Atlit (IL)

(73) Assignee: DEXCEL PHARMA TECHNOLOGIES LTD., Jerusalem (IL)

( * ) Notice: Subject to any disclaimer, the term of this patent is extended or adjusted under 35 U.S.C. 154(b) by 303 days.

This patent is subject to a terminal disclaimer.

(21) Appl. No.: 17/389,612

(22) Filed: Jul. 30, 2021

(65) Prior Publication Data

US 2021/0353535 A1    Nov. 18, 2021

Related U.S. Application Data

(63) Continuation of application No. 15/238,109, filed on Aug. 16, 2016, now Pat. No. 11,077,055, which is a continuation of application No. PCT/IL2016/050425, filed on Apr. 21, 2016.

(60) Provisional application No. 62/154,250, filed on Apr. 29, 2015.

(51) Int. Cl.
| | |
|---|---|
| *A61K 31/4439* | (2006.01) |
| *A61K 9/00* | (2006.01) |
| *A61K 9/16* | (2006.01) |
| *A61K 9/20* | (2006.01) |
| *A61K 9/28* | (2006.01) |
| *A61K 9/50* | (2006.01) |
| *A61K 31/4184* | (2006.01) |

(52) U.S. Cl.
CPC .......... *A61K 9/0056* (2013.01); *A61K 9/1623* (2013.01); *A61K 9/1676* (2013.01); *A61K 9/2072* (2013.01); *A61K 9/2081* (2013.01); *A61K 9/2086* (2013.01); *A61K 9/28* (2013.01); *A61K 9/2886* (2013.01); *A61K 9/5026* (2013.01); *A61K 9/5042* (2013.01); *A61K 9/5047* (2013.01); *A61K 9/5078* (2013.01); *A61K 31/4184* (2013.01); *A61K 31/4439* (2013.01)

(58) Field of Classification Search
None
See application file for complete search history.

(56) References Cited

U.S. PATENT DOCUMENTS

| | | |
|---|---|---|
| 2,757,124 A | 7/1956 | Wolff |
| 4,045,563 A | 8/1977 | Berntsson |
| 4,255,431 A | 3/1981 | Junggren |
| 4,359,465 A | 11/1982 | Ruwart |
| 4,472,409 A | 9/1984 | Senn-Bilfinger |
| 4,508,905 A | 4/1985 | Junggren |
| 4,547,359 A | 10/1985 | Zierenberg |
| 4,628,098 A | 12/1986 | Nohara |
| 4,666,703 A | 5/1987 | Kopf |
| 4,689,333 A | 8/1987 | Nohara |
| 4,710,384 A | 12/1987 | Rotman |
| 4,738,974 A | 4/1988 | Brandstrom |
| 4,738,975 A | 4/1988 | Nohara |
| 4,749,575 A | 6/1988 | Rotman |
| 4,786,505 A | 11/1988 | Lovgren |
| 4,840,799 A | 6/1989 | Appelgren |
| 4,853,230 A | 8/1989 | Lovgren |
| 4,874,614 A | 10/1989 | Becker |
| 4,888,178 A | 12/1989 | Rotini |
| 4,940,588 A | 7/1990 | Sparks |
| 4,950,484 A | 8/1990 | Olthoff |
| 5,006,344 A | 4/1991 | Jerzewski |
| 5,013,557 A | 5/1991 | Tai |
| 5,013,743 A | 5/1991 | Iwahi |
| 5,026,560 A | 6/1991 | Makino |
| 5,045,321 A | 9/1991 | Makino |
| 5,045,552 A | 9/1991 | Souda |
| 5,055,306 A | 10/1991 | Barry |
| 5,073,374 A | 12/1991 | McCarty |
| 5,093,132 A | 3/1992 | Makino |
| 5,215,756 A | 6/1993 | Gole |
| 5,219,870 A | 6/1993 | Kim |
| 5,232,706 A | 8/1993 | Palomo Coll |
| 5,244,670 A | 9/1993 | Upson et al. |
| 5,288,506 A | 2/1994 | Spickett |
| 5,312,824 A | 5/1994 | Sohda |
| 5,362,424 A | 11/1994 | Lee |
| 5,385,739 A | 1/1995 | Debregeas |
| 5,399,700 A | 3/1995 | Min |
| 5,409,711 A | 4/1995 | Mapelli et al. |
| 5,433,959 A | 7/1995 | Makino |
| 5,464,632 A | 11/1995 | Cousin |
| 5,508,041 A | 4/1996 | Lee |
| 5,518,730 A | 5/1996 | Fuisz |
| 5,554,147 A | 9/1996 | Batich |
| 5,582,837 A | 12/1996 | Shell |

(Continued)

FOREIGN PATENT DOCUMENTS

| | | |
|---|---|---|
| CN | 1961868 A | 5/2007 |
| DE | 19752843 | 7/1999 |

(Continued)

OTHER PUBLICATIONS

Prevacid 24HR (lansoprazole 15 mg) Delayed Release Capsule, NDA 22-327, Medical Review, (2009), 5 pages.

(Continued)

*Primary Examiner* — Tigabu Kassa
(74) *Attorney, Agent, or Firm* — ROTHWELL, FIGG, ERNST & MANBECK, P.C.

(57) ABSTRACT

An orally disintegrating dosage form of a proton pump inhibitor, methods for its production and use thereof are provided. The dosage form includes a plurality of pellets containing a proton pump inhibitor admixed with a disintegrant to afford rapid disintegration in the oral cavity after administration.

13 Claims, No Drawings

(56) References Cited

U.S. PATENT DOCUMENTS

| | | |
|---|---|---|
| 5,622,717 A | 4/1997 | Fuisz |
| 5,626,875 A | 5/1997 | Ballester Rodes |
| 5,639,478 A | 6/1997 | Makino |
| 5,690,960 A | 11/1997 | Bengtsson |
| 5,708,017 A | 1/1998 | Dave |
| 5,731,002 A | 3/1998 | Olovson |
| 5,753,265 A | 5/1998 | Bergstrand |
| 5,780,057 A | 7/1998 | Conte |
| 5,783,215 A | 7/1998 | Arwidsson |
| 5,788,678 A | 8/1998 | Van Antwerp |
| 5,798,120 A | 8/1998 | Tomohisa |
| 5,807,583 A | 9/1998 | Kristensen |
| 5,814,338 A | 9/1998 | Veronesi |
| 5,817,338 A | 10/1998 | Bergstrand |
| 5,824,339 A | 10/1998 | Shimizu |
| 5,840,737 A | 11/1998 | Phillips |
| 5,855,914 A | 1/1999 | Koyama |
| 5,869,098 A | 2/1999 | Misra |
| 5,879,708 A | 3/1999 | Makino |
| 5,900,424 A | 5/1999 | Kallstrom |
| 5,945,124 A | 8/1999 | Sachs |
| 5,968,551 A | 10/1999 | Oshlack |
| 5,972,389 A | 10/1999 | Shell |
| 5,985,322 A | 11/1999 | Anderson |
| 5,997,903 A | 12/1999 | Dietrich |
| 6,013,281 A | 1/2000 | Lundberg |
| 6,017,560 A | 1/2000 | Makino |
| 6,022,562 A | 2/2000 | Autant |
| 6,068,856 A | 5/2000 | Sachs |
| 6,077,541 A | 6/2000 | Chen |
| 6,090,827 A | 7/2000 | Erickson |
| 6,096,340 A | 8/2000 | Chen |
| 6,113,941 A | 9/2000 | Takada |
| 6,123,962 A | 9/2000 | Makino et al. |
| 6,132,770 A | 10/2000 | Lundberg |
| 6,132,771 A | 10/2000 | Depui |
| 6,136,344 A | 10/2000 | Depui |
| 6,149,942 A | 11/2000 | Scheiwe |
| 6,159,499 A | 12/2000 | Seth |
| 6,165,512 A | 12/2000 | Mezaache |
| 6,174,548 B1 | 1/2001 | Chen |
| 6,183,776 B1 | 2/2001 | Depui |
| 6,207,198 B1 | 3/2001 | Seth |
| 6,228,400 B1 | 5/2001 | Lee |
| 6,231,888 B1 | 5/2001 | Lerner |
| 6,248,355 B1 | 6/2001 | Seth |
| 6,248,758 B1 | 6/2001 | Klokkers |
| 6,270,804 B1 | 8/2001 | Getz |
| 6,274,173 B1 | 8/2001 | Sachs |
| 6,284,271 B1 | 9/2001 | Lundberg |
| 6,294,192 B1 | 9/2001 | Patel |
| 6,296,875 B1 | 10/2001 | Makino |
| 6,296,876 B1 | 10/2001 | Odidi |
| 6,316,029 B1 | 11/2001 | Jain |
| 6,328,994 B1 | 12/2001 | Simizu |
| 6,344,215 B1 | 2/2002 | Bettman et al. |
| 6,346,269 B1 | 2/2002 | Hsiao |
| 6,365,184 B1 | 4/2002 | Depui |
| 6,372,254 B1 | 4/2002 | Ting |
| 6,379,705 B1 | 4/2002 | Mendes |
| 6,380,234 B1 | 4/2002 | Makino |
| 6,383,471 B1 | 5/2002 | Chen |
| 6,391,342 B1 | 5/2002 | Henriksen |
| 6,395,300 B1 | 5/2002 | Straub |
| 6,403,616 B1 | 6/2002 | Erickson |
| 6,426,369 B1 | 7/2002 | Sato |
| 6,428,809 B1 | 8/2002 | Abrams |
| 6,428,810 B1 | 8/2002 | Bergstand |
| 6,479,075 B1 | 11/2002 | Odidi |
| 6,489,346 B1 | 12/2002 | Phillips |
| 6,489,646 B1 | 12/2002 | Phillips |
| 6,500,459 B1 | 12/2002 | Chhabra |
| 6,544,556 B1 | 4/2003 | Chen |
| 6,551,621 B1 | 4/2003 | Debregeas |
| 6,569,453 B2 | 5/2003 | Linder |
| 6,576,258 B1 | 6/2003 | Kofler |
| 6,586,004 B2 | 7/2003 | Shimizu |
| 6,589,556 B2 | 7/2003 | Cherukuri |
| 6,596,315 B1 | 7/2003 | Boissier |
| 6,599,529 B1 | 7/2003 | Skinhoej et al. |
| 6,602,522 B1 | 8/2003 | Chen |
| 6,605,303 B1 | 8/2003 | Karehill |
| 6,610,323 B1 | 8/2003 | Lundberg |
| 6,613,354 B2 | 9/2003 | Depui |
| 6,623,759 B2 | 9/2003 | Heese |
| 6,627,219 B2 | 9/2003 | Hao |
| 6,627,223 B2 | 9/2003 | Percel |
| 6,638,534 B1 | 10/2003 | Ishibashi |
| 6,645,528 B1 | 11/2003 | Straub |
| 6,645,988 B2 | 11/2003 | Phillips |
| 6,521,256 B2 | 12/2003 | Makino |
| 6,699,885 B2 | 3/2004 | Phillips |
| 6,706,285 B1 | 3/2004 | Woo |
| 6,713,079 B2 | 3/2004 | Usala |
| 6,720,001 B2 | 4/2004 | Chen |
| 6,726,927 B2 | 4/2004 | Chen |
| 6,730,685 B1 | 5/2004 | Brulls |
| 6,733,778 B1 | 5/2004 | Chen |
| 6,740,339 B1 | 5/2004 | Ohkouchi |
| 6,749,864 B2 | 6/2004 | Makino |
| 6,749,867 B2 | 6/2004 | Robinson |
| 6,780,435 B2 | 8/2004 | Chen |
| 6,780,436 B1 | 8/2004 | Lopez-Cabrera |
| 6,780,881 B2 | 8/2004 | Linder |
| 6,780,882 B2 | 8/2004 | Phillips |
| 6,855,336 B2 | 2/2005 | Chen |
| 6,869,615 B2 | 3/2005 | Chen |
| 6,884,437 B2 | 4/2005 | Linder |
| 6,897,205 B2 | 5/2005 | Beckert |
| 6,923,988 B2 | 8/2005 | Patel |
| 6,932,983 B1 | 8/2005 | Straub |
| 6,960,357 B2 | 11/2005 | Chopra |
| 6,962,717 B1 | 11/2005 | Huber |
| 6,982,281 B1 | 1/2006 | Chen et al. |
| 7,041,316 B2 | 5/2006 | Chen |
| 7,070,805 B2 | 7/2006 | Shimizu |
| 7,105,180 B2 | 9/2006 | Schmitt |
| 7,147,869 B2 | 12/2006 | Dietrich |
| 7,217,429 B2 | 5/2007 | Garcia |
| 7,223,421 B2 | 5/2007 | McTeigue |
| 7,255,878 B1 | 8/2007 | Lahav |
| 7,351,723 B2 | 4/2008 | Linder |
| 7,399,485 B1 | 7/2008 | Shimizu |
| 7,431,942 B2 | 10/2008 | Shimizu |
| 7,476,403 B2 | 1/2009 | Li |
| 7,674,837 B2 | 3/2010 | Gaserod et al. |
| 7,732,474 B2 | 6/2010 | Muskulus |
| 7,749,533 B2 | 7/2010 | Fu |
| 7,815,940 B2 | 10/2010 | Pettersson |
| 7,838,033 B2 | 11/2010 | Tanaka |
| 7,875,292 B2 | 1/2011 | Shimizu |
| 7,943,167 B2 | 5/2011 | Kulkarni et al. |
| 7,951,398 B2 | 5/2011 | Dietrich |
| 8,093,271 B2 | 1/2012 | Los |
| 8,101,209 B2 | 1/2012 | Legrand |
| 8,105,626 B2 | 1/2012 | Shimizu |
| 8,173,158 B2 | 5/2012 | Lee |
| 8,187,617 B2 | 5/2012 | Howard |
| 8,303,868 B2 | 11/2012 | Maruyama |
| 8,329,744 B2 | 12/2012 | Babul |
| 8,343,978 B2 | 1/2013 | Dong |
| 8,383,154 B2 | 2/2013 | Bar-Shalom |
| 8,409,612 B1 | 4/2013 | Criere |
| 8,449,911 B2 | 5/2013 | Yoneyama |
| 8,486,450 B2 | 7/2013 | Higuchi |
| 8,530,463 B2 | 9/2013 | Cartt et al. |
| 8,545,881 B2 | 10/2013 | Venkatesh et al. |
| 8,685,448 B2 | 4/2014 | Santanach-Delisau |
| 8,697,097 B2 | 4/2014 | Nonomura |
| 8,715,730 B2 | 5/2014 | Takaki |
| 8,765,176 B2 | 7/2014 | Yamamoto |
| 8,771,729 B2 | 7/2014 | Perrett et al. |
| 8,846,698 B2 | 9/2014 | Andrews et al. |
| 8,865,212 B2 | 10/2014 | Ghosh |

(56) References Cited

U.S. PATENT DOCUMENTS

| | | | |
|---|---|---|---|
| 8,871,273 B2 | 10/2014 | Nagahara | |
| 8,877,746 B2 | 11/2014 | Chen | |
| 8,883,206 B2 | 11/2014 | Dokou | |
| 8,911,787 B2 | 12/2014 | Gandhi | |
| 8,968,776 B2 | 3/2015 | Seth | |
| 8,980,322 B2 | 3/2015 | Nagahara | |
| 8,993,599 B2 | 3/2015 | Hall | |
| 8,999,384 B2 | 4/2015 | Shafee | |
| 9,060,936 B2 | 6/2015 | Berndl | |
| 9,186,409 B2 * | 11/2015 | Larsen | A61K 9/0065 |
| 9,198,862 B2 | 12/2015 | Pilgaonkar | |
| 9,241,910 B2 | 1/2016 | Kurasawa | |
| 9,486,446 B2 | 11/2016 | Kurasawa | |
| 9,526,789 B2 | 12/2016 | Park | |
| 2001/0024658 A1 | 9/2001 | Chen | |
| 2001/0053387 A1 | 12/2001 | Hamied | |
| 2002/0004071 A1 | 1/2002 | Cherukuri | |
| 2002/0039597 A1 | 4/2002 | Ukai | |
| 2002/0039598 A1 | 4/2002 | Makino | |
| 2002/0045646 A1 | 4/2002 | Phillips | |
| 2002/0086029 A1 | 7/2002 | Lundberg et al. | |
| 2002/0098242 A1 | 7/2002 | Dardar | |
| 2002/0128293 A1 | 9/2002 | Rampal | |
| 2002/0137771 A1 | 9/2002 | Makino | |
| 2002/0142034 A1 | 10/2002 | Shimizu | |
| 2002/0147208 A1 | 10/2002 | Fleshner-Barak | |
| 2002/0155067 A1 | 10/2002 | MacGregor | |
| 2002/0160046 A1 | 10/2002 | Robinson | |
| 2003/0096791 A1 | 5/2003 | Gupte | |
| 2003/0113376 A1 | 6/2003 | Chen | |
| 2003/0211155 A1 | 11/2003 | Makino | |
| 2003/0219479 A1 | 11/2003 | Chen | |
| 2004/0018235 A1 | 1/2004 | Tanizawa et al. | |
| 2004/0028737 A1 | 2/2004 | Deshpande | |
| 2004/0029777 A1 | 2/2004 | Ando | |
| 2004/0109894 A1 | 6/2004 | Shefer | |
| 2004/0126422 A1 | 7/2004 | Tony Yu | |
| 2004/0131675 A1 | 7/2004 | Yamamoto | |
| 2004/0166162 A1 | 8/2004 | Niecestro et al. | |
| 2004/0185111 A1 | 9/2004 | Rubino | |
| 2004/0202714 A1 | 10/2004 | Nomura | |
| 2004/0209919 A1 | 10/2004 | Makino | |
| 2004/0213847 A1 | 10/2004 | Matharu | |
| 2004/0219211 A1 | 11/2004 | Criere | |
| 2004/0248942 A1 | 12/2004 | Hepburn | |
| 2005/0043300 A1 | 2/2005 | Middleton et al. | |
| 2005/0053655 A1 | 3/2005 | Yang | |
| 2005/0095285 A1 | 5/2005 | Rao | |
| 2005/0095293 A1 | 5/2005 | Brauns | |
| 2005/0106237 A1 | 5/2005 | Wuthrich et al. | |
| 2005/0112193 A1 | 5/2005 | Phillips | |
| 2005/0136112 A1 | 6/2005 | Gonzales | |
| 2005/0147668 A1 | 7/2005 | Bertelsen et al. | |
| 2005/0191353 A1 | 9/2005 | Krishna Antarkar | |
| 2005/0214371 A1 | 9/2005 | Di Capua | |
| 2005/0214372 A1 | 9/2005 | Di Capua et al. | |
| 2005/0232988 A1 | 10/2005 | Venkatesh | |
| 2005/0232992 A1 | 10/2005 | Devane | |
| 2005/0287211 A1 | 12/2005 | Yoshida | |
| 2006/0018964 A1 | 1/2006 | Combessis | |
| 2006/0051421 A1 | 3/2006 | Shterman | |
| 2006/0078614 A1 | 4/2006 | Venkatesh | |
| 2006/0105039 A1 | 5/2006 | Lai | |
| 2006/0115530 A1 | 6/2006 | Pettersson | |
| 2006/0134210 A1 | 6/2006 | Perrson | |
| 2006/0153908 A1 | 7/2006 | Strong | |
| 2006/0153918 A1 | 7/2006 | Lerner | |
| 2006/0159762 A1 | 7/2006 | Stanic Ljubin | |
| 2006/0177509 A1 | 8/2006 | Nagahara | |
| 2006/0204568 A1 | 9/2006 | Dietrich | |
| 2006/0216346 A1 | 9/2006 | Dietrich | |
| 2006/0222701 A1 | 10/2006 | Kulkarni et al. | |
| 2006/0240100 A1 | 10/2006 | Anstett | |
| 2006/0240103 A1 | 10/2006 | McCallister et al. | |
| 2006/0257467 A1 | 11/2006 | Kostadinov | |
| 2006/0276500 A1 | 12/2006 | Phillips | |
| 2007/0053981 A1 | 3/2007 | Blychert | |
| 2007/0065513 A1 | 3/2007 | Ayramoff | |
| 2007/0141151 A1 | 6/2007 | Silver | |
| 2007/0148153 A1 | 6/2007 | Shlieout | |
| 2007/0202169 A1 | 8/2007 | Silver et al. | |
| 2007/0231388 A1 | 10/2007 | Anstett-Klein | |
| 2007/0259040 A1 | 11/2007 | Cherukuri | |
| 2008/0003281 A1 | 1/2008 | Clemmensen | |
| 2008/0014228 A1 | 1/2008 | Darmuzey | |
| 2008/0014257 A1 | 1/2008 | He | |
| 2008/0026051 A1 | 1/2008 | Lizio | |
| 2008/0033027 A1 | 2/2008 | Bascomb | |
| 2008/0050428 A1 | 2/2008 | Ney | |
| 2008/0063710 A1 | 3/2008 | Suzuki | |
| 2008/0069878 A1 | 3/2008 | Venkatesh et al. | |
| 2008/0095853 A1 | 4/2008 | Clemmensen | |
| 2008/0102133 A1 | 5/2008 | Brueck-Scheffler | |
| 2008/0145421 A1 | 6/2008 | Ukai | |
| 2008/0193522 A1 | 8/2008 | Meier | |
| 2008/0214619 A1 | 9/2008 | Wolfe et al. | |
| 2008/0226684 A1 | 9/2008 | Peppas | |
| 2008/0254112 A1 | 10/2008 | Klokkers | |
| 2008/0254115 A1 | 10/2008 | Rubino | |
| 2008/0305160 A1 | 12/2008 | Guimberteau | |
| 2008/0305166 A1 | 12/2008 | During | |
| 2008/0312168 A1 | 12/2008 | Pilgaonkar | |
| 2009/0068263 A1 | 3/2009 | Antarkar | |
| 2009/0148524 A1 | 6/2009 | Higuchi et al. | |
| 2009/0208576 A1 | 8/2009 | Gandhi et al. | |
| 2009/0220611 A1 | 9/2009 | Dargelas | |
| 2009/0220613 A1 | 9/2009 | Odidi | |
| 2009/0291136 A1 | 11/2009 | Stanic Ljubin | |
| 2009/0304787 A1 | 12/2009 | Odidi | |
| 2010/0015239 A1 | 1/2010 | Ahmed | |
| 2010/0016382 A1 | 1/2010 | Nomura | |
| 2010/0068268 A1 | 3/2010 | Rahmouni | |
| 2010/0080849 A1 | 4/2010 | Schlutermann | |
| 2010/0130542 A1 | 5/2010 | Phillips | |
| 2010/0172969 A1 | 7/2010 | Dreu et al. | |
| 2010/0221324 A1 | 9/2010 | Petereit | |
| 2010/0247641 A1 | 9/2010 | Ranzani | |
| 2010/0255091 A1 | 10/2010 | Ranzani | |
| 2010/0260854 A1 | 10/2010 | Rossi et al. | |
| 2010/0286400 A1 | 11/2010 | Urakami et al. | |
| 2010/0297226 A1 | 11/2010 | Penhasi | |
| 2010/0316709 A1 | 12/2010 | Kurasawa | |
| 2011/0045068 A1 | 2/2011 | Valducci | |
| 2011/0091563 A1 | 4/2011 | Kurasawa | |
| 2011/0135722 A1 | 6/2011 | Criere | |
| 2011/0177164 A1 | 7/2011 | Rajan | |
| 2011/0177165 A1 | 7/2011 | Gerber | |
| 2011/0189271 A1 | 8/2011 | Lad | |
| 2011/0223244 A1 | 9/2011 | Liversidge | |
| 2011/0229562 A1 | 9/2011 | Bar | |
| 2011/0229570 A1 | 9/2011 | Sugimoto | |
| 2011/0236475 A1 | 9/2011 | Pasha | |
| 2011/0281912 A1 | 11/2011 | Winter | |
| 2011/0293715 A1 | 12/2011 | Combessis | |
| 2011/0311595 A1 | 12/2011 | Berndi | |
| 2011/0311631 A1 | 12/2011 | Baer | |
| 2012/0004321 A1 | 1/2012 | Hoashi | |
| 2012/0027822 A1 | 2/2012 | Politis | |
| 2012/0040001 A1 | 2/2012 | Koizumi | |
| 2012/0045506 A1 | 2/2012 | Baer | |
| 2012/0077888 A1 | 3/2012 | Ramtoola | |
| 2012/0082721 A1 | 4/2012 | Buessing | |
| 2012/0093926 A1 | 4/2012 | Bodinge | |
| 2012/0128764 A1 | 5/2012 | Venkatesh | |
| 2012/0141584 A1 | 6/2012 | Chauhan | |
| 2012/0219628 A1 | 8/2012 | Lim | |
| 2012/0282335 A1 | 11/2012 | Venkatesh | |
| 2012/0321702 A1 | 12/2012 | Encina Garcia | |
| 2013/0122090 A1 | 5/2013 | Borude | |
| 2013/0189360 A1 | 7/2013 | Sakamoto | |
| 2013/0202688 A1 | 8/2013 | Roy | |
| 2013/0216617 A1 | 8/2013 | Roy et al. | |
| 2013/0243859 A1 | 9/2013 | Mima et al. | |
| 2013/0266658 A1 | 10/2013 | Wei | |

(56) References Cited

U.S. PATENT DOCUMENTS

| | | |
|---|---|---|
| 2013/0273157 A1 | 10/2013 | Ishii |
| 2013/0274243 A1 | 10/2013 | Bagal et al. |
| 2014/0248341 A1 | 9/2014 | Liversidge et al. |
| 2014/0248350 A1 | 9/2014 | Reyes |
| 2014/0255503 A1 | 9/2014 | Perez |
| 2014/0287051 A1 | 9/2014 | Perrett et al. |
| 2014/0296191 A1 | 10/2014 | Patel et al. |
| 2014/0309219 A1 | 10/2014 | Chang et al. |
| 2014/0314846 A1 | 10/2014 | Penhasi |
| 2014/0343049 A1 | 11/2014 | Toueg et al. |
| 2015/0005232 A1 | 1/2015 | Cheruvallath et al. |
| 2015/0031693 A1 | 1/2015 | McKew et al. |
| 2015/0037423 A1 | 2/2015 | Kurasawa et al. |
| 2015/0038510 A1 | 2/2015 | Lawson et al. |
| 2015/0104512 A1 | 4/2015 | Ognibene |
| 2015/0216806 A1 | 8/2015 | Borody |
| 2015/0225405 A1 | 8/2015 | Cheruvallah |
| 2015/0225412 A1 | 8/2015 | Brameld |
| 2015/0272889 A1 | 10/2015 | Hoashi |
| 2015/0283085 A1 | 10/2015 | Venkatesh |
| 2015/0297642 A1 | 10/2015 | Borody |
| 2016/0089338 A1 | 3/2016 | Kawano |
| 2016/0279071 A1 | 9/2016 | Park |
| 2016/0346274 A1 | 12/2016 | Vaka |
| 2016/0354356 A1 | 12/2016 | Moses-Heller |
| 2016/0368908 A1 | 12/2016 | Owens |
| 2017/0119660 A1 | 5/2017 | Temtsin-Krayz |
| 2017/0183359 A1 | 6/2017 | Ishida |
| 2017/0298046 A1 | 10/2017 | Soldano |
| 2019/0046459 A1 | 2/2019 | Kim |

FOREIGN PATENT DOCUMENTS

| | | |
|---|---|---|
| EP | 0 377 518 A2 | 7/1990 |
| EP | 0 768 082 A1 | 4/1997 |
| EP | 0519144 | 8/1997 |
| EP | 0567201 B1 | 9/1999 |
| EP | 1 813 275 A1 | 8/2007 |
| EP | 1834634 | 9/2007 |
| EP | 1837016 | 9/2007 |
| EP | 2600847 | 6/2013 |
| EP | 2641594 | 9/2013 |
| GB | 2067900 | 8/1981 |
| GB | 2 245 492 A | 1/1992 |
| IN | 1679/MUM/2010 | 2/2013 |
| JP | 2009256344 A | 11/2009 |
| WO | 98/32426 A | 7/1998 |
| WO | WO1999027917 | 6/1999 |
| WO | 00/18376 A | 4/2000 |
| WO | WO2000035448 | 6/2000 |
| WO | WO2000078293 | 12/2000 |
| WO | 01/58447 A1 | 8/2001 |
| WO | WO2003086343 | 10/2003 |
| WO | WO2004052607 | 6/2004 |
| WO | WO2004098573 | 11/2004 |
| WO | WO2005034924 | 4/2005 |
| WO | WO2005058282 | 6/2005 |
| WO | WO2006011159 | 2/2006 |
| WO | WO2006026829 | 3/2006 |
| WO | 2006058250 A2 | 6/2006 |
| WO | WO2006067599 | 6/2006 |
| WO | WO2006116582 | 11/2006 |
| WO | 2007/016563 A2 | 2/2007 |
| WO | WO2007070164 | 6/2007 |
| WO | 2007/078271 A2 | 7/2007 |
| WO | 2007/093642 A2 | 8/2007 |
| WO | WO2008047320 | 4/2008 |
| WO | WO2008140459 | 11/2008 |
| WO | 2009022670 A1 | 2/2009 |
| WO | WO2009036811 | 3/2009 |
| WO | WO2010018593 | 2/2010 |
| WO | WO2010022944 | 3/2010 |
| WO | WO2010034344 | 4/2010 |
| WO | WO2010056059 | 5/2010 |
| WO | WO2010105672 | 9/2010 |
| WO | WO2010105673 | 9/2010 |
| WO | WO2010116385 | 10/2010 |
| WO | WO2010122583 | 10/2010 |
| WO | WO2011039768 | 4/2011 |
| WO | 2011080502 A2 | 7/2011 |
| WO | WO2011111027 | 9/2011 |
| WO | WO2011112709 | 9/2011 |
| WO | WO2011140446 | 11/2011 |
| WO | WO2011144975 | 11/2011 |
| WO | 2012017074 A1 | 2/2012 |
| WO | WO2012022498 | 2/2012 |
| WO | WO2012092486 | 7/2012 |
| WO | WO2013100705 | 7/2013 |
| WO | WO2013122413 | 8/2013 |
| WO | 2013140120 A1 | 9/2013 |
| WO | WO2013156088 | 10/2013 |
| WO | WO2013175511 | 11/2013 |
| WO | WO2013183497 | 12/2013 |
| WO | WO2013186311 | 12/2013 |
| WO | WO2014016754 | 1/2014 |
| WO | WO2014032741 | 3/2014 |
| WO | WO2014032742 | 3/2014 |
| WO | WO2014046312 | 3/2014 |
| WO | WO2014079922 | 5/2014 |
| WO | 2015181059 A1 | 12/2015 |
| WO | WO2015151059 | 12/2015 |
| WO | 2016092387 | 6/2016 |
| WO | 2016155786 | 10/2016 |
| WO | 2017150803 A1 | 9/2017 |

OTHER PUBLICATIONS

Prevacid 24HR (lansoprazole 15 mg) Delayed Release Capsule, product label, 2010, 3 pages.

Guidance for Industry Orally Disintegrating Tablets. U.S. Department of Health and Human Services; Food and Drug Administration; Center for Drug Evaluation and Research (CDER). Dec. 2008, Chemistry, 6 pages.

35(3) Harmonization Stage 6: 429 Light Diffraction Measurement of Particle Size; (2016); 8 pages.

Extended European Search Report issued for European Patent Application No. 16786065.9 dated Aug. 22, 2018, 11 pages.

Medical Review, Appl. No. 208025Orig1s000, "Lansoprazole Delayed-Release Orally-Disintegrating Tablets", Center for Drug Evaluation and Research, Dec. 4, 2015, 84 pages.

Shimizu et al., Chemical and pharmaceutical bulletin, (2003) vol. 51(8). pp. 942-947.

Shimizu et al., Chemical and pharmaceutical bulletin, (2003) vol. 51(9). pp. 1029-1035.

Shimizu et al., Chemical and pharmaceutical bulletin, (2003) vol. 51(10). pp. 1121-1127.

U.S. Pharmacopeial Convention, "<1216> Tablet friability," Aug. 1, 2016, p. 1609.

U.S. Pharmacopeial Convention, "<701> Disintegration," Aug. 1, 2008, 3 pages.

Fabio Baldi et al., "Lansoprazole Fast Disintegrating Tablet: A New Formulation for an Established Proton Pump Inhibitor", Digestion 2003, 67, pp. 1-5, DOI: 10.1159/000070393.

National Center for Biotechnology information, PubChem Compound Summary for CID 2724691, Sodium Stearate. Retrieved Oct. 30, 2023, from https://pubchem.ncbi.nlm.nih.gov/compound/Sodium-Stearate. (2023), 47 pages.

Andrews et al., American Journal of Veterinary Research, (1999) vol. 60( 8), pp. 929-931.

Choudhury et al., Indian Journal of Pharmaceutical Sciences, (2010) vol. 72( 4), pp. 491-494.

Colome et al., Journal of Drug Delivery Science and Technology, (2007) vol. 17( 2), pp. 113-118.

Farinha et al., Druge Development and Industrial Pharmacy, (2000) vol. 26(7), pp. 785-790.

Ito et al., International Journal of Pharmaceutics, (2005) vol. 286(1-2), pp. 69-77.

Jedinger et al., European Jornal of Pharmaceutics and Biopharmaceutics, (2014) vol. 87, pp. 217-226.

(56) References Cited

OTHER PUBLICATIONS

Kamath et al., International Journal of Pharmacy and Pharmaceutical Sciences, (2012) vol. 4(33), pp. 257-367.
Lehmann et al., Drugs Made in Germany, (1994) vol. 37(2), pp. 53-60.
Raffin, Pharmazie, (2007) vol. 62(5), pp. 361-364.
U.S. Pharmacopeia <1216>.
U.S. Pharmacopeia <701>.

* cited by examiner

ORALLY DISINTEGRATING COMPOSITIONS

CROSS REFERENCE TO RELATED APPLICATION

This application is a continuation of U.S. patent application Ser. No. 15/238,109, filed Aug. 16, 2016, which is a continuation of PCT/IL2016/050425, filed Apr. 21, 2016, which claims the benefit of U.S. Patent Application No. 62/154,250 filed on Apr. 29, 2015, the disclosure of which are incorporated herein in its entirety by reference.

TECHNICAL FIELD

An orally disintegrating dosage form comprising a proton pump inhibitor, methods for its production and use thereof are provided.

BACKGROUND

Orally disintegrating compositions have gained considerable attention as an alternative to conventional tablets and capsules. These compositions, which are also referred to as orodisperse formulations, usually afford the rapid disintegration of the constituents therein in the oral cavity in less than 60 seconds. Orally disintegrating compositions provide improved patient compliance, particularly in patients who experience difficulties swallowing conventional dosage forms such as pediatric and geriatric patients, subjects who suffer from impaired swallowing and subjects who suffer from psychiatric disorders.

Proton pump inhibitors (PPIs) are potent inhibitors of gastric acid secretion by specific inhibition of the $H^+/K^+$-ATPase enzyme system at the secretory surface of the gastric parietal cells. PPIs are typically benzimidazole derivatives such as omeprazole, lansoprazole and pantoprazole. U.S. Pat. Nos. 4,045,563; 4,255,431; 4,359,465; 4,472,409; 4,508,905; 4,628,098; 4,738,975; 4,786,505; 4,853,230; 5,045,321; 5,045,552; and 5,312,824 disclose benzimidazole compounds which can be used as proton pump inhibitors.

PPIs are known to be susceptible to degradation and transformation in acidic media. When in contact with the stomach content, which is highly acidic, these compounds become degraded. Accordingly, formulations containing PPIs typically include an enteric coating layer which is designed to protect the active ingredients during their passage through the stomach.

Enteric coating materials are polymers which contain acidic functional groups capable of being ionized at elevated pH values. At low pH values (e.g. the acidic environment of the stomach), the enteric polymers are not ionized, and therefore, insoluble. As the pH increases (e.g. when entering the small intestine), the acidic functional groups ionize and the polymer becomes soluble. Thus, an enteric coating allows a delayed release of the active substance and the absorption of the same through the intestinal mucosa.

Enteric coating materials are mainly composed of cellulose, vinyl, and acrylic derivatives which are known to dissolve in the presence of alcohol. Consumption of enteric coated compositions along with alcohol adversely affects the gastro-resistance of the enteric coating material and may further induce dose dumping which is characterized by unintended release of the active substance. Dose dumping may also lead to fluctuations in the concentration of the active substance in the body thereby posing a serious safety concern and, in some instances, may also lead to lack of therapeutic efficacy of the drug.

WO 2014/032741 discloses a gastric resistant pharmaceutical or nutraceutical composition with resistance against the influence of ethanol comprising a) a core, comprising a pharmaceutical or a nutraceutical active ingredient, b) an inner coating layer comprising at least 30% by weight of one or more salts of alginic acid, and c) an outer coating layer comprising at least 30% by weight of one or more polymers or copolymers comprising anionic side groups.

WO 2012/022498 discloses a gastric resistant pharmaceutical or nutraceutical composition comprising a core, comprising a pharmaceutical or nutraceutical active ingredient and a gastric resistant coating layer onto the core, wherein the release of the pharmaceutical or nutraceutical active ingredient is not more than 15% under in-vitro conditions at pH 1.2 for 2 hours in medium according to USP with and without the addition of 40% (v/v) ethanol, wherein the gastric resistant coating layer comprises 10 to 100% by weight of one or more salts of alginic acid with a viscosity of 30 to 720 cP of a 1% aqueous solution.

WO 2011/039768 discloses a pharmaceutical composition comprising a core comprising an active substance or a salt thereof; a separating layer comprising at least one sugar; and a functional layer comprising at least one pharmaceutically acceptable polymer, wherein the composition is resistant to dose dumping in presence of alcohol.

WO 2010/105673 and WO 2010/105672 disclose controlled release pharmaceutical compositions with resistance against the influence of ethanol employing a coating comprising vinyl polymers.

WO 2009/036811 and WO 2010/034344 disclose a pH-dependent controlled release pharmaceutical composition, comprising at least one pharmaceutical active ingredient, with the exception of opioids, wherein the core is coated at least by one coating layer, controlling the release of the pharmaceutical composition, wherein the coating layer comprises a polymer mixture of neutral vinyl polymer or copolymer and an anionic polymer or copolymer. The composition is resistant against the influence of ethanol.

WO 2011/112709 discloses an alcohol-resistant pharmaceutical composition comprising i) an active agent; ii) an enteric system; and iii) an alcohol protectant in an amount sufficient to prevent release of the active agent in the presence of alcohol.

Thus far, only a limited number of robust dosage forms that withstand the impact of alcohol are available and the development of such dosage forms is still challenging.

There is an unmet need for orally disintegrating compositions comprising a PPI which afford reduced risk of alcohol induced dose dumping.

SUMMARY

The present disclosure relates to orally disintegrating compositions comprising a therapeutically effective amount of a proton pump inhibitor (PPI), wherein after administration, the composition substantially disintegrates in the oral cavity of a subject within less than about 60 seconds. The composition provides a release profile of the active ingredient which is substantially the same as the release profile of a conventional non-orally disintegrating composition in the absence of alcohol while showing markedly improved resistance to dose dumping in the presence of alcohol. The present disclosure further relates to methods of preparing said orally disintegrating compositions and use thereof in the treatment or prevention of, inter alia, peptic ulcers.

The present disclosure is based, in part, on the unexpected finding of a PPI formulation which is an orally disintegrating formulation, preferably an orally disintegrating tablet, and which provides improved resistance to alcohol induced dose dumping. It was not previously realized that enteric coated active cores which are resistant to alcohol induced dose dumping can be compressed into orally disintegrating tablets without losing their alcohol resistance characteristics. The advantage of using orally disintegrating dosage forms, for example high compliance with the end-user, can be maintained while still affording resistance to alcohol induced dose dumping.

According to a first aspect, there is provided an orally disintegrating composition comprising (i) enteric coated active cores comprising a therapeutically effective amount of a proton pump inhibitor, and (ii) at least one pharmaceutically acceptable excipient comprising a disintegrant, wherein the composition substantially disintegrates in the oral cavity of a subject in need thereof within less than about 60 seconds after administration, and wherein in vitro drug release in 15 minutes at 0.1N HCl and 40% ethanol is less than about 20%.

In certain embodiments, the orally disintegrating composition substantially 20 disintegrates in the oral cavity of a subject in need thereof within less than about seconds after administration.

In further embodiments, the orally disintegrating composition provides a release profile of the PPI which is substantially the same as the release profile of a non-orally disintegrating composition in the absence of alcohol. In accordance with these embodiments, the orally disintegrating composition results in a $C_{max}$ or AUC after administration which is substantially equivalent to a non-orally disintegrating composition comprising a PPI in the absence of alcohol. In specific embodiments, the orally disintegrating composition disclosed herein provides a release profile of the PPI in the presence of up to 40% ethanol which is substantially the same as the release profile of the composition in the absence of alcohol thereby being substantially resistant to alcohol induced dose dumping.

In one embodiment, the active cores comprise a plurality of inert seeds coated with a therapeutically effective amount of a proton pump inhibitor. In another embodiment, the active cores comprise a plurality of units comprising a therapeutically effective amount of a proton pump inhibitor embedded in a matrix. In yet another embodiment, the active cores comprise a plurality of units comprising a first portion of a proton pump inhibitor embedded in a matrix and a second portion of a proton pump inhibitor coating said units, wherein the first and second portions of the proton pump inhibitor together constitute a therapeutically effective amount of the proton pump inhibitor.

In several embodiments, the proton pump inhibitor comprises lansoprazole, omeprazole, pantoprazole, leminoprazole, perprazole, rabeprazole, or a pharmaceutically acceptable salt thereof.

It is contemplated that any pharmaceutically acceptable form of the proton pump inhibitor including, but not limited to, salts (e.g. alkaline salts), solvates (e.g. hydrates), isomers, isomorphs, polymorphs, pseudopolymorphs, and prodrugs thereof are within the scope of the present disclosure.

In one embodiment, the proton pump inhibitor comprises a proton pump inhibitor salt.

In another embodiment, the proton pump inhibitor comprises a proton pump inhibitor enantiomer.

In further embodiments, the proton pump inhibitor comprises a salt of a proton pump inhibitor enantiomer.

In particular embodiments, the proton pump inhibitor comprises lansoprazole or a pharmaceutically acceptable salt thereof.

In certain embodiments, the inert seeds comprise sugar spheres. In other embodiments, the inert seeds comprise microcrystalline cellulose particles.

In some embodiments, the active cores may further comprise at least one excipient such as a binder, a filler, a surfactant, and any combination thereof.

In particular embodiments, the active cores may further comprise an alkalizing agent.

In various embodiments, the active cores are coated with enteric coating comprising one or more enteric polymers selected from the group consisting of cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, polymethacrylic acid, polymethyl methacrylate, and polyethyl methacrylate, with each possibility representing a separate embodiment. In one embodiment, the active cores are coated with enteric coating comprising hydroxypropyl methylcellulose phthalate.

In certain aspects and embodiments, the active cores are further coated with a subcoating layer over the active cores, to protect the enteric coating, once applied, from reacting with the alkaline active cores containing the proton pump inhibitor. In some embodiments, the subcoating layer comprises at least one of hydroxypropyl methylcellulose, hydroxypropyl cellulose, polyvinylpyrrolidone, polyethylene glycol, and polyvinyl alcohol with each possibility representing a separate embodiment.

In additional embodiments, the enteric coated active cores may optionally comprise an additional taste-masking layer over the enteric coating, the taste-masking layer comprising a substantially water-insoluble taste-masking polymer. In particular embodiments, the substantially water-insoluble taste-masking polymer is selected from the group consisting of ethyl cellulose, polyvinyl acetate (PVA), cellulose acetate (CA), cellulose acetate butyrate (CAB), and methacrylate copolymers including dimethylaminoethyl methacrylate, butyl methacrylate, methyl methacrylate copolymers such as those available under the trade name "Eudragit®" (e.g. Eudragit® RL, Eudragit® RS, Eudragit® E, Eudragit® NE30D, etc.). Each possibility represents a separate embodiment of the disclosure.

In further embodiments, the enteric coated active cores may optionally comprise an additional over-coating layer which may be layered over the enteric coating or over the taste-masking layer, the over-coating layer comprising at least one of hydroxypropyl methylcellulose, hydroxypropyl cellulose, polyvinylpyrrolidone, polyethylene glycol, and polyvinyl alcohol with each possibility representing a separate embodiment.

It will be recognized by one of skill in the art that each of the coating layers may further comprise a plasticizer, a surfactant, a filler, a lubricant, an anti-tacking agent or a combination thereof, with each possibility representing a separate embodiment.

In certain embodiments, there is provided an orally disintegrating composition comprising at least one excipient comprising a disintegrant.

In exemplary embodiments, the disintegrant is selected from the group consisting of crospovidone (cross-linked PVP), croscarmelose sodium, a sugar alcohol, a cellulose derivative, cross-linked derivatives of starch, pregelatinized starch and any combination or mixture thereof, with each possibility representing a separate embodiment.

In some embodiments, the sugar alcohol is selected from the group consisting of mannitol, sorbitol, maltitol, xylitol, and any combination or mixtures thereof. Each possibility represents a separate embodiment.

In other embodiments, the cellulose derivative is selected from the group consisting of methylcellulose, cross-linked carboxymethyl cellulose, cross-linked sodium carboxymethyl cellulose, microcrystalline cellulose, low substituted hydroxypropyl cellulose and any combination or mixtures thereof. Each possibility represents a separate embodiment.

In yet other embodiments, the cross-linked derivatives of starch comprise sodium starch glycolate.

In further embodiments, the orally disintegrating composition disclosed herein comprises a plurality of excipients as compression additives, the plurality of excipients comprising a disintegrant and at least one of a binder, a filler, an anti-tacking agent, a lubricant, a glidant, a surfactant, a plasticizer or any combination thereof, with each possibility representing a separate embodiment.

In some embodiments, there is provided an orally disintegrating composition in the form of an orally disintegrating tablet. In accordance with these embodiments, the orally disintegrating tablet is characterized by hardness of at least 20 Newtons, for example about 20-80 Newtons, about 30-70 Newtons, or about 40-60 Newtons. Each possibility represents a separate embodiment.

In specific embodiments, the orally disintegrating composition described herein comprises: (a) inert seeds in an amount of about 2% to about 10% by weight of the total composition; (b) a proton pump inhibitor in an amount of about 3% to about 9% by weight of the total composition; (c) a subcoating layer in an amount of about 5% to about 15% by weight of the total composition; (d) an enteric coating in an amount of about 10% to about 25% by weight of the total composition; (e) at least one disintegrant in an amount of about 2% to about 15% by weight of the total composition; and (f) optionally one or more additional excipients selected from a binder, a filler, an anti-tacking agent, an alkalizing agent, a lubricant, a glidant, a surfactant, a plasticizer and any combination thereof in an amount of not more than about 30% by weight of the total composition, wherein presence of all components add to 100% (w/w).

The orally disintegrating pharmaceutical composition of the present disclosure is useful for inhibiting gastric acid secretion in the treatment of gastroesophageal reflux disease, gastritis, peptic ulcers (duodenal and gastric) and erosive esophagitis, with each possibility representing a separate embodiment.

Accordingly, there is provided a method of inhibiting gastric acid secretion, the method comprising administering to a subject in need thereof the orally disintegrating composition disclosed herein. In other embodiments, there is provided a method of treating a disease or disorder selected from the group consisting of gastroesophageal reflux disease, gastritis, peptic ulcers (duodenal and gastric) and erosive esophagitis, the method comprising administering to a subject in need thereof the orally disintegrating composition disclosed herein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

There is provided an orally disintegrating dosage form such as, but not limited to, an orally disintegrating tablet (ODT) comprising a therapeutically effective amount of a proton pump inhibitor that enables fast disintegration of the composition in the oral cavity. The orally disintegrating dosage form is particularly suitable for subjects who may be incapable of, or are having difficulties in swallowing. The orally disintegrating dosage form is substantially resistant to alcohol induced dose dumping. Contrary to dosage forms that are inserted into capsules for oral administration through the gastrointestinal tract, the composition disclosed herein is designed to disintegrate in the oral cavity of a subject in need thereof. Even though the pH in the oral cavity is similar to the pH of the upper intestine, where the enteric coating disintegrates to release the active ingredient, the enteric coating used in the disclosed composition maintains its integrity in the oral cavity and when passing through the stomach in the absence/presence of alcohol such that it affords the delayed release of the active ingredient in the upper intestine.

According to certain aspects and embodiments, there is provided a composition comprising a therapeutically effective amount of a proton pump inhibitor, wherein the composition rapidly disintegrates in the oral cavity after oral administration. In particular embodiments, the composition is in a form of an orally disintegrating tablet. As used herein, the term "orally disintegrating composition" or "orally disintegrating dosage form" refers to a composition that disintegrates in the oral cavity of the subject in need thereof upon coming into contact with the mucosal tissue of the tongue, cheek, and/or mouth within a short period of time, for example in less than about 60 seconds, preferably in less than about 30 seconds after administration. Upon administration of the orally disintegrating pharmaceutical composition to the oral cavity of a subject in need thereof, the composition disintegrates rapidly into the subject's oral cavity to form a smooth suspension of particles that can be readily swallowed.

According to some embodiments, the orally disintegrating composition provides a release profile of the proton pump inhibitor which is substantially the same as the release profile of a conventional composition which is not an orally disintegrating composition in the absence of alcohol. As used herein, the term "substantially the same" refers to a release profile of the orally disintegrating composition disclosed herein which varies in less than about 20%, for example, about 15%, about 10%, about 5% or is substantially identical to the release profile of a non-orally disintegrating composition which contains about the same dosage of the proton pump inhibitor. As used herein, the term "release profile" refers to in vitro release in an appropriate testing medium as well as to in vivo release so that the orally disintegrating composition disclosed herein is substantially bioequivalent to a conventional composition which is a non-orally disintegrating composition containing about the same dosage of the proton pump inhibitor in the absence of alcohol. It is contemplated that the composition disclosed herein results in a $C_{max}$ or AUC after administration which is substantially equivalent to a conventional composition which is not an orally disintegrating composition in the absence of alcohol. As used herein, the term "a conventional composition which is not an orally disintegrating composition" refers to an oral dosage form which is designed to be swallowed as a whole e.g. swallowable tablets and capsules.

In some aspects and embodiments, the orally disintegrating composition provides a release profile of the PPI in the presence of alcohol which is substantially the same as the release profile of the composition in the absence of alcohol. In other words, the composition provided herein is substantially resistant to alcohol induced dose dumping. As used herein, the term "alcohol induced dose dumping" refers to undesired release of the active ingredient when taken together with alcohol. The term "resistant to alcohol induced dose dumping" as used herein refers to a composition which provides in vitro drug release in 15 minutes at 0.1N hydrochloric acid (HCl) and 40% ethanol (v/v) of less than about 20%, for example about 15%, about 10%, about 5% or about 0%. Alternatively, this term refers to a composition which provides not more than about 20%, for example about 15%, about 10%, about 5% or about 0% of active compound being released when the composition is exposed to 0.1N hydrochloric acid (HCl) and 40% ethanol (v/v) for 15 minutes in paddle dissolution apparatus at 100 rpm. In one embodiment, the test is performed in 300 ml of 0.1N HCl and 40% ethanol (v/v). In another embodiment, the test is performed in 500 ml of 0.1N HCl and 40% ethanol (v/v). In yet another embodiment, the test is performed in 900 ml of 0.1N HCl and 40% ethanol (v/v). It is contemplated that the composition disclosed herein results in a $C_{max}$ or AUC after administration which are superior to a conventional composition which is not an orally disintegrating composition in the presence of alcohol.

The orally disintegrating composition according to the principles described herein provides unexpected resistance to alcohol induced dose dumping. Surprisingly, it is now being disclosed that enteric coated active cores (also referred to herein as pellets) which are resistant to alcohol induced dose dumping can be admixed with at least one pharmaceutical excipient comprising a disintegrant and compressed into orally disintegrating compositions (e.g. tablets) without adversely affecting their resistance to alcohol induced dose dumping. The orally disintegrating composition thus obtained is characterized by having an enteric layer with superior mechanical properties such that it substantially maintains its integrity at compression while still affording resistance to alcohol induced dose dumping. Moreover, the formed composition is sufficiently hard (e.g. tablets which are characterized by hardness of at least 20 Newtons, e.g. about 20-80 Newtons, about 30-70 Newtons, or about 40-60 Newtons) while still allowing disintegration in the oral cavity in less than about 60 seconds.

The proton pump inhibitors suitable as being incorporated in the orally-disintegrating compositions include, but are not limited to, lansoprazole, omeprazole, pantoprazole, leminoprazole, perprazole, and rabeprazole. Each possibility represents a separate embodiment of the disclosure.

It is contemplated that any pharmaceutically acceptable form of the proton pump inhibitor including, but not limited to, salts (e.g. alkali metal or alkaline earth metal salts such as omeprazole magnesium), solvates (e.g. hydrates), isomers (e.g. enantiomers such as dexlansoprazole or esomeprazole), isomorphs, polymorphs, pseudopolymorphs, and prodrugs thereof are within the scope of the present disclosure.

In various embodiments, the proton pump inhibitor is present in the composition as a racemic mixture. In other embodiments, the proton pump inhibitor is present in the composition as a single enantiomeric form. In another embodiment, the proton pump inhibitor is present in the composition as a salt. In further embodiments, the proton pump inhibitor is present in the composition as an alkaline earth metal salt of the PPI such as, but not limited to, a calcium or magnesium salt. In several embodiments, the proton pump inhibitor is present in the composition as an amorphous form. In other embodiments, the proton pump inhibitor is present in the composition as a crystalline form.

According to certain aspects and embodiments, there is provided an orally disintegrating composition comprising a mixture of enteric coated active cores and at least one pharmaceutically acceptable excipient comprising a disintegrant. As used herein, the term "active cores" refers to a plurality of units comprising a therapeutically effective amount of a proton pump inhibitor. The units may be in any form known to those of skill in the art such as, but not limited to, granules, spheroids, beads and the like. In certain embodiments, the units comprise a therapeutically effective amount of a proton pump inhibitor embedded in a matrix of pharmaceutically acceptable excipients. In other embodiments, the units comprise a first portion of a proton pump inhibitor embedded in a matrix as described herein which are further coated with a second portion of a proton pump inhibitor so that the combination of the first and second portions constitute a therapeutically effective amount of the proton pump inhibitor. The units comprising a proton pump inhibitor embedded in a matrix may be formed, for example, by extrusion and/or spheronization as is known in the art. In some embodiments, the units comprise inert seeds which are coated with a layer (also referred to herein as a drug layer) comprising a therapeutically effective amount of a proton pump inhibitor.

The inert seeds of the compositions described herein can be comprised of any pharmaceutically inert compound, e.g., a filler. The inert seeds onto which the layer of the active ingredient is applied are usually comprised of sugars, starch or cellulosic materials or combinations thereof, for example sugar derivatives such as lactose, sucrose, hydrolyzed starch (maltodextrins) or celluloses or mixtures thereof. In one embodiment, the inert seeds comprise nonpareils comprising a blend of starch and sugar. The nonpareils, also called sugar spheres, typically comprise spheres composed of sucrose and starch (for example, maize starch). In another embodiment, the inert seeds comprise microcrystalline cellulose particles. Other types of seeds may also be used.

In order to stabilize the drug substance, which is susceptible to degradation in acidic environment, the proton pump inhibitor may be admixed with an alkalizing agent. Suitable alkalizing agents include, but are not limited to, organic and inorganic alkaline substances. Suitable organic alkaline substances include, but are not limited to, basic amino acids such as arginine and lysine, amine derivatives and salts, amino sugars such as meglumine, salts of stearic acid such as sodium stearate and the like, with each possibility representing a separate embodiment. Suitable inorganic alkaline agents include, but are not limited to, hydroxides such as sodium or potassium hydroxide, carbonates such as calcium, magnesium or zinc carbonate and the like, with each possibility representing a separate embodiment.

Within the scope of the present disclosure are enteric coated active cores which are preferably coated with subcoating over the drug layer or drug matrix to separate the active cores from the enteric coating. The subcoating is typically layered between the core containing a therapeutically effective amount of a proton pump inhibitor and the enteric coating to afford physical separation between the alkaline core containing a therapeutically effective amount of a proton pump inhibitor and the acidic enteric coating.

Suitable subcoating comprises at least one of hydroxypropyl methylcellulose, hydroxypropyl cellulose, polyvinylpyrrolidone, polyethylene glycol, and polyvinyl alcohol, with each possibility representing a separate embodiment. In some embodiments, the subcoating does not contain alginic acid salts or derivatives thereof.

Suitable enteric coating includes, but is not limited to, cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, polymethacrylic acid, polymethyl methacrylate, and polyethyl methacrylate, with each possibility representing a separate embodiment. In certain embodiments, the enteric coating does not contain vinyl polymers or derivatives thereof. In other embodiments, the enteric coating does not contain alginic acid salts or derivatives thereof. In exemplary embodiments, the enteric coating is selected from the group consisting of cellulose acetate phthalate (CAP), hydroxypropyl methylcellulose phthalate (HPMCP), hydroxypropyl methylcellulose acetate succinate (HPMCAS), cellulose acetate trimellitate, polymethacrylic acid, polymethyl methacrylate, and polyethyl methacrylate, with each possibility representing a separate embodiment. In particular embodiments, the enteric coating comprises hydroxypropyl methylcellulose phthalate (HPMCP). It is contemplated that a single enteric coating layer comprised of a single enteric polymer is sufficient to impart the composition of the present disclosure its beneficial attributes.

The enteric coated active cores may optionally comprise an additional taste-masking layer over the enteric coating. A taste-masking layer may be applied in order to improve the organoleptic characteristics of the composition, such that the taste and mouth feel of the disintegrated composition remain acceptable to a subject until the contents of the dosage form are swallowed, usually without water or other fluids. Typically, the contents of the composition remain in the oral cavity for several minutes (e.g. 2-3 minutes) until they are swallowed. In certain embodiments, the taste-masking layer comprises a substantially water-insoluble polymer including, but not limited to, ethyl cellulose, polyvinyl acetate (PVA), cellulose acetate (CA), cellulose acetate butyrate (CAB), and methacrylate copolymers including dimethylaminoethyl methacrylate, butyl methacrylate, methyl methacrylate copolymers and the like. Commercially available polymers suitable for taste-masking include, but are not limited to, "Eudragit®" polymers such as Eudragit® RL, Eudragit® RS, Eudragit® E, Eudragit® NE30D, etc., with each possibility representing a separate embodiment. In particular embodiments, the taste-masking layer comprises at least one of a cellulose derivative, an acrylate based polymer, PVA or any other polymer currently used for this purpose, with each possibility representing a separate embodiment.

The enteric coated active cores may optionally comprise an additional over-coating layer which may be layered over the enteric coating or the taste masking layer, with each possibility representing a separate embodiment. The over-coating layer may comprise at least one of hydroxypropyl methylcellulose, hydroxypropyl cellulose, polyvinylpyrrolidone, polyethylene glycol, and polyvinyl alcohol, with each possibility representing a separate embodiment.

It is contemplated that each of the coating layers may further comprise a plastisizer, a surfactant, a filler, a lubricant, an anti-tacking agent or a combination thereof. In certain embodiment, these substances may be added to the coating layer(s) to facilitate the application of the coating layer(s) onto the substrate.

The pellets of the orally disintegrating composition described herein are admixed with at least one excipient comprising a disintegrant. In some embodiments, the pellets are admixed with a plurality of excipients (i.e. compression additives) comprising at least one disintegrant. The pellets as well as the pharmaceutically acceptable excipient(s) typically have average sizes of less than about 1,000 μm, for example about 100-900 m, about 200-800 μm, about 300-700 μm, or about 400-600 μm thereby affording reduced sensation of roughness when disintegrated in the oral cavity. Each possibility represents a separate embodiment.

Suitable disintegrants within the scope of the present disclosure include, but are not limited to, crospovidone, croscarmelose sodium, a sugar alcohol, a cellulose derivative, cross-linked derivatives of starch (e.g. sodium starch glycolate), pregelatinized starch, cross-linked sodium carboxymethyl cellulose, low substituted hydroxypropylcellulose and any combination or mixture thereof, with each possibility representing a separate embodiment. Additional disintegrants include, but are not limited to, silicates, carbonates, polyoxyethylene sorbitan fatty acid esters, stearic monoglyceride, guar gum, and lactose. Each possibility represents a separate embodiment. Suitable sugar alcohols include, but are not limited to, mannitol, sorbitol, maltitol, xylitol, and any combination or mixtures thereof. Each possibility represents a separate embodiment. Additional sugar alcohols include, but are not limited to, arabitol, isomalt, erythritol, glycerol, lactitol, and any combination or mixtures thereof. Each possibility represents a separate embodiment. Suitable cellulose derivatives include, but are not limited to, methylcellulose, cross-linked carboxymethyl celluloses, microcrystalline cellulose and any combination or mixtures thereof. Each possibility represents a separate embodiment.

According to the principles disclosed herein, the orally disintegrating compositions may further comprise at least one additional excipient such as a binder, a filler, an anti-tacking agent, a lubricant, a glidant, a surfactant, a plasticizer or any combination thereof as is known in the art. Each possibility represents a separate embodiment. The excipient(s) may be added to the pellets for example applied together with the therapeutically effective amount of the proton pump inhibitor, the subcoating, enteric coating, taste-masking layer and/or over-coating and/or the excipient(s) may be admixed with the pellets and the at least one disintegrant to form the compositions disclosed herein. Each possibility represents a separate embodiment.

Suitable binders include, but are not limited to, polyvinylpyrrolidone, copovidone, hydroxypropylmethyl cellulose, starch, gelatin, or sugars. Sugars include sucrose, dextrose, molasses, and lactose. Each possibility represents a separate embodiment.

Suitable fillers include, but are not limited to, sugars such as lactose, sucrose, mannitol or sorbitol and derivatives therefore (e.g. amino sugars), ethylcellulose, microcrystalline cellulose, silicified microcrystalline cellulose and the like. Each possibility represents a separate embodiment.

Suitable anti-tacking agents include, but are not limited to, magnesium stearate, calcium stearate, stearic acid, talc, colloidal silicon and the like among others. Each possibility represents a separate embodiment.

Suitable lubricants include, but are not limited to, sodium stearyl fumarate, stearic acid, polyethylene glycol or stearates, such as magnesium stearate. Each possibility represents a separate embodiment.

A suitable glidant within the scope of the present disclosure is e.g., colloidal silicon dioxide.

Suitable surfactants include, but are not limited to, non-ionic, anionic or cationic surfactants. Typically, surfactants may have one lipophilic and one hydrophilic group in the molecule. The surfactant may optionally comprise one or more of soaps, detergents, emulsifiers, dispersing and wetting agents. More specifically, surfactants may optionally comprise, for example, one or more of polysorbate, stearyltriethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose among others. Each possibility represents a separate embodiment.

Suitable plasticizers include, but are not limited to, cetyl alcohol, dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol among others. Each possibility represents a separate embodiment.

The orally disintegrating compositions may further comprise additional excipients in the pellets and/or admixed with the pellets and the at least one disintegrant such as stabilizers, tonicity enhancing agents, buffering substances, preservatives, thickeners, diluents, emulsifying agents, wetting agents, flavoring agents, colorants, and complexing agents as is known in the art.

Suitable tonicity enhancing agents are selected from ionic and non-ionic agents. For example, ionic compounds include, but are not limited to, alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. Each possibility represents a separate embodiment.

Examples of preservatives are quaternary ammonium salts such as benzalkonium chloride, benzoxonium chloride or polymeric quaternary ammonium salts, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sorbic acid or ascorbic acid. Each possibility represents a separate embodiment.

Suitable diluents include, but are not limited to, dicalcium phosphate dihydrate, sugars, lactose, calcium phosphate, cellulose, kaolin, mannitol, sodium chloride, and dry starch. Each possibility represents a separate embodiment.

Suitable wetting agents include, but are not limited to, glycerin, starches, and the like. Each possibility represents a separate embodiment.

Suitable buffering substances include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide. Each possibility represents a separate embodiment.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide. Each possibility represents a separate embodiment.

Suitable flavoring agents include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, eucalyptus, vanilla, citrus oil such as lemon oil, orange oil, grape and grapefruit oil, and fruit essences including apple, peach, pear, strawberry, raspberry, cherry, plum, pineapple, and apricot. Each possibility represents a separate embodiment.

In specific embodiments, the orally disintegrating composition comprises: (a) inert seeds in an amount of about 2% to about 10% by weight of the total composition; (b) a proton pump inhibitor in an amount of about 3% to about 9% by weight of the total composition; (c) a subcoating layer in an amount of about 5% to about 15% by weight of the total composition; (d) an enteric coating in an amount of about 10% to about 25% by weight of the total composition; (e) at least one disintegrant in an amount of about 2% to about 15% by weight of the total composition; and (f) optionally one or more additional excipients selected from a binder, a filler, an anti-tacking agent, an alkalizing agent, a lubricant, a glidant, a surfactant, a plasticizer or any combination thereof in an amount of not more than about 30% by weight of the total composition, wherein presence of all components add to 100%. In certain embodiments, the orally disintegrating composition comprises at least one alkalizing agent in an amount of about 1% to about 5% by weight of the total composition typically admixed with the proton pump inhibitor.

In some embodiments, the orally disintegrating composition is an orally disintegrating tablet that comprises:
  enteric coated active cores that include inert seeds, a drug coating layer, a subcoating layer, an enteric coating layer, and optionally a taste-masking layer and/or an over-coating layer,
    inert seeds comprise a filler, e.g. sugar spheres and/or microcrystalline cellulose particles;
    the drug coating layer covering the inert seeds comprises a proton-pump inhibitor, e.g. lansoprazole; an alkalizing agent, e.g. meglumine; a binder, e.g. hydroxypropylmethyl cellulose (HPMC) and/or polyvinylpyrrolidone (PVP); and optionally a surfactant, e.g. polysorbate; and/or a filler, e.g. mannitol;
    the subcoating layer covering the drug coating layer comprises a binder, e.g. hydroxypropylmethyl cellulose (HPMC) and/or polyvinylpyrrolidone (PVP); an anti-tacking agent, e.g. talc; and optionally a surfactant, e.g. polysorbate and/or a filler, e.g. mannitol;
    the enteric coating layer covering the subcoating layer comprises one or more enteric coating polymers, e.g.

hydroxypropyl methylcellulose phthalate (HPMCP); an anti-tacking agent, e.g. talc; a plasticizer, e.g. cetyl alcohol and/or triethyl citrate; and optionally a colorant, e.g. titanium dioxide;

optional taste-masking layer covering the enteric coating comprises a taste-masking polymer, e.g. a methacrylate-based copolymer; and a gildant, e.g. colloidal silicon dioxide;

the optional over-coating layer covering the enteric coating or the taste-masking layer comprises a binder, e.g. hydroxypropylmethyl cellulose (HPMC) and/or polyvinylpyrrolidone (PVP); an anti-tacking agent, e.g. talc; and optionally a surfactant, e.g. polysorbate and/or a filler, e.g. mannitol; and one or more disintegrants, e.g. crospovidone; and optionally one or more preservatives, e.g. ascorbic acid; one or more flavoring agents, e.g. strawberry flavor; and/or one or more lubricants, e.g. sodium stearyl fumarate; blended with the enteric coated active cores and compressed into a tablet.

The orally disintegrating compositions can be manufactured using conventional processes as is known in the art such as, but not limited to, spheronization, milling, de-agglomeration, precipitation, and/or crystallization. Each possibility represents a separate embodiment. Exemplary method of preparing an orally disintegrating tablet (ODT) according to the principles disclosed herein comprises the following steps: (a) applying a dispersion or solution of a proton pump inhibitor and optionally a pharmaceutically acceptable excipient comprising an alkalizing agent onto a plurality of inert seeds to obtain active cores; (b) optionally applying a subcoating onto the active cores; (c) applying an enteric coating onto the active cores obtained in step (a) or (b); (d) optionally applying a taste-masking layer and/or an over-coating layer onto the enteric coated active cores obtained in step (c); (e) blending the enteric coated active cores obtained in step (c) or (d) with particles comprising at least one excipient comprising a disintegrant; and (f) compressing the mixture obtained in step (e) into an orally disintegrating tablet as is known in the art. Optionally, the method of preparing the orally disintegrating composition involves additional processing steps including, but not limited to heating, drying, sieving, lubricating and packaging as is known in the art. The various coatings may be applied to the seeds/cores in the form of an organic or aqueous solution or dispersion, with each possibility representing a separate embodiment. The application of the coatings (e.g. drug layer, subcoating, enteric coating, taste-masking, over-coating etc.) may be performed as is known in the art using standard equipment such as, but not limited to, a fluid bed coater (e.g. a Wurster coater or a rotary bed coater), extruder, or spray dryer. When using spray coating technique, various apparatus may be employed including, but not limited to, rotary disks, single-fluid high pressure swirl nozzles, two-fluid nozzles or ultrasonic nozzles, Single stage dryer, Two stage dryer, Horizontal dryer, Fluidized spray coater (e.g., TURBOJET), Multi stage drier, Compact spray dryer, Integrated filter drier, FILTERMAT® dryer, including, e.g., Glatt, Gea-Niro, BWI Huttlin, and Allgaier among others, with each possibility representing a separate embodiment.

The orally disintegrating pharmaceutical composition is useful for inhibiting gastric acid secretion. In certain embodiments, the orally disintegrating pharmaceutical composition is useful in the treatment of gastroesophageal reflux disease, gastritis, peptic ulcers (duodenal and gastric) or erosive esophagitis, with each possibility representing a separate embodiment.

Accordingly, there is provided a method of inhibiting gastric acid secretion in the treatment of a disease or disorder selected from gastroesophageal reflux disease, gastritis, peptic ulcers (duodenal and gastric) and erosive esophagitis, the method comprising administering to a subject in need thereof the orally disintegrating composition disclosed herein. In some embodiments, the method further comprises the disintegration of the composition in the oral cavity of the subject to provide a plurality of particles comprising enteric coated active cores as described herein, the method further comprises the release of a majority of the proton-pump inhibitor from the enteric coated active cores in the upper intestine.

The subject in need thereof is typically a mammal, preferably a human. The orally disintegrating composition may be administered in a solid dosage form to be placed on the tongue (lingual administration), or under the tongue (sublingual administration), or applied to the buccal mucosa (buccal administration). Lingual administration typically stimulates saliva generation, which enhances disintegration of the composition. In some embodiments, the composition is a dosage form suitable for forming a suspension of undissolved particles in saliva, which can then be swallowed, allowing for absorption of the active ingredient in the GI tract, generally in the upper intestine. The amount of a composition to be administered depends on various factors including the subject being treated (age and gender) and the severity of the disease, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as the age of the patient and the presence of other diseases or conditions. The orally disintegrating compositions may contain any dosage of the proton pump inhibitor, for example from about 2 mg to about 50 mg of the active ingredient such as, but not limited to, 5 mg, 10 mg, 20 mg, 30 mg or 40 mg, with each possibility representing a separate embodiment.

The term "therapeutically effective amount" or "an effective amount" as used herein refers to a quantity of a compound which is sufficient to provide a beneficial effect to the subject to which the compound is administered. The effective amount, according to the principles disclosed herein can be determined by any one of ordinary skill in the art and can be tested on various models both in vitro and in vivo.

The term "treating" as used herein refers to stopping or slowing down the progression of the disease. The term "treating" further includes the reduction in the occurrence of various symptoms associated with gastric acid secretion.

As used herein and in the appended claims, the term "about" refers to ±10%.

As used herein and in the appended claims, the singular forms "a", "an", and "the" include plural references unless the context clearly dictates otherwise. Thus, for example, reference to "a layer" includes a plurality of such layers and equivalents thereof known to those skilled in the art, and so forth. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

An orally disintegrating tablet was prepared as follows: Inert sugar spheres or microcrystalline cellulose particles were coated with a drug layer containing 15, 15.5 or 30 mg lansoprazole and typically further containing a binder (e.g. hydroxypropyl methylcellulose, i.e. HPMC or hypromellose) and an alkalizing agent (e.g. meglumine). A subcoating layer containing hypromellose and typically an anti-tacking agent (e.g. talc), and an enteric coating layer containing enteric polymer such as hypromellose phthalate, hypromellose acetate succinate or metacrylic acid copolymer and typically further containing a plasticizer (e.g. triethyl citrate) and an anti-tacking agent (e.g. talc) were then sequentially applied. An over-coating layer containing polyvinyl pyrrolidone was optionally applied. The enteric coated active cores were blended with a mixture of powders containing crospovidone, Pharmaburst®, microcrystalline cellulose or croscarmellose sodium as disintegrant, lubricated (e.g. with sodium stearyl fumarate) and compressed into orally disintegrating tablets.

Exemplary formulations of the present disclosure are outlined in Tables 1-5 below:

TABLE 1

| Substance | Mg/tab |
| --- | --- |
| Lansoprazole | 30.0 |
| Sugar Spheres | 42.4 |
| Mannitol fine | 33.2 |
| Meglumine | 9.4 |
| Polysorbate (Tween-80) | 9.8 |
| Hypromellose (HPMC E5) | 36.7 |
| Talc micronized | 9.5 |
| Hypromellose Phthalate (HP50) | 54.8 |
| Cetyl alcohol | 9.8 |
| Triethyl citrate (TEC) | 4.5 |
| Titanium dioxide | 1.1 |
| Pharmaburst ® | 203.0 |
| Crospovidone (Kollidon CL) | 16.1 |
| Sucralose micronized | 7.2 |
| Ascorbic acid | 5.2 |
| Pulv. mint extra 1013044 flavor | 3.6 |
| Silica colloidal anhydrous | 2.4 |
| Sodium stearyl fumarate | 3.6 |
| Total | 482.3 |

TABLE 2

| Substance | Mg/tab |
| --- | --- |
| Lansoprazole | 15.5 |
| Microcrystalline cellulose (MCC) particles | 62.5 |
| Polysorbate 80 (Tween 80) | 6.1 |
| Lactose DCL11 | 19.9 |
| Hydroxypropyl methylcellulose (HPMC) 2910/5 (Methocel E5) | 19.9 |
| Meglumine | 5.2 |
| Hydroxypropyl methylcellulose acetate succinate | 149.8 |
| Polyvinylpyrrolidone (PVP) | 7.1 |
| Polyethylene glycol (PEG) | 4.5 |
| Croscarmellose sodium | 7.1 |
| Mannitol | 50.8 |

TABLE 2-continued

| Substance | Mg/tab |
| --- | --- |
| Sorbitol | 16.7 |
| Microcrystalline cellulose (Avicel) | 31.6 |
| Acesulfame K | 3.3 |
| Total | 400 |

TABLE 3

| Substance | Mg/tab |
| --- | --- |
| Lansoprazole | 30.0 |
| Sugar Spheres | 42.0 |
| Hypromellose (HPMC E5) | 36.6 |
| Mannitol fine | 33.0 |
| Meglumine | 9.2 |
| Polysorbate (Tween-80) | 9.4 |
| Talc micronized | 12.1 |
| Hypromellose Phthalate (HP55S) | 80.0 |
| Cetyl alcohol | 14.4 |
| Triethyl citrate (TEC) | 6.7 |
| Titanium dioxide | 1.6 |
| Pharmaburst ® | 194.0 |
| Crospovidone | 20.6 |
| Copovidone Fine | 12.0 |
| Sucralose | 0.9 |
| Ascorbic Acid | 4.7 |
| Strawberry flavor | 2.4 |
| Colloidal Silicon Dioxide | 2.8 |
| Sodium Stearyl Fumarate | 3.6 |
| Total | 516 |

TABLE 4

| Substance | Mg/tab |
| --- | --- |
| Lansoprazole | 15.0 |
| Sugar Spheres | 21.0 |
| Mannitol fine | 16.5 |
| Meglumine | 4.6 |
| Polysorbate (Tween-80) | 4.7 |
| Hypromellose (HPMC E5) | 18.3 |
| Talc micronized | 5.1 |
| Hypromellose Phthalate (HP55) | 30.2 |
| Cetyl alcohol | 5.5 |
| Triethyl citrate (TEC) | 2.5 |
| Titanium dioxide | 0.6 |
| Pharmaburst ® | 108.5 |
| Crospovidone (Kollidon CL) | 8.3 |
| Sucralose micronized | 0.5 |
| Ascorbic acid | 2.3 |
| Strawberry AP52311 | 1.2 |
| Silica colloidal anhydrous | 1.3 |
| Sodium stearyl fumarate | 1.9 |
| Total | 248 |

TABLE 5

| Substance | Mg/tab |
| --- | --- |
| Lansoprazole | 30.0 |
| Sugar Spheres | 44.2 |
| Mannitol fine | 32.5 |
| Meglumine | 9.2 |
| Polysorbate (Tween-80) | 9.6 |
| Hypromellose (HPMC E5) | 36.0 |
| Talc micronized | 16.9 |
| Hypromellose Phthalate (HP50) | 131.4 |
| Cetyl alcohol | 23.6 |
| Triethyl citrate (TEC) | 10.7 |

TABLE 5-continued

| Substance | Mg/tab |
|---|---|
| Titanium dioxide | 2.7 |
| Pharmaburst ® | 291.9 |
| Crospovidone (Kollidon CL) | 22.9 |
| Sucralose micronized | 10.4 |
| Ascorbic acid | 7.6 |
| Pulv. mint extra 1013044 flavor | 5.2 |
| Silica colloidal anhydrous | 3.5 |
| Sodium stearyl fumarate | 5.2 |
| Total | 693.5 |

Example 2

Friability and disintegration of an exemplary orally disintegrating tablet were tested according to US Pharmacopeia <1216> and <701>, respectively. The average results are presented in Table 6:

TABLE 6

| Response | Acceptable ranges | Results | | |
|---|---|---|---|---|
| Friability (%) | NMT 1.0% | 0% | 0% | 0.22% |
| Disintegration (sec) | NMT 60 sec | 23 seconds | 30 seconds | 17 seconds |

Example 3

An in vitro alcohol-induced dose dumping study was conducted on an exemplary orally disintegrating tablet using 0.1N HCl with 5%, 20% and 40% (v/v) of ethanol (App. 2 (paddles); 100 rpm; 500 ml). Data was collected every 15 minutes for a total of 1 hour.

The drug release at each level of alcohol (added to 0.1N HCl) was tested on an orally disintegrating tablet containing 15 mg lansoprazole. Control testing was performed using Prevacid® 24 HR capsules containing 15 mg lansoprazole. The results are depicted in Table 7:

TABLE 7

| | | Drug release | |
|---|---|---|---|
| Medium | Time (min) | ODT of the present disclosure | Prevacid ® 24 HR capsules |
| HCl 0.1N + 5% ethanol | 15 | 2% | 4% |
| | 30 | 3% | 5% |
| | 45 | 4% | 5% |
| | 60 | 5% | 5% |
| HCl 0.1N + 20% ethanol | 15 | 1% | 1% |
| | 30 | 3% | 2% |
| | 45 | 5% | 3% |
| | 60 | 13% | 8% |
| HCl 0.1N + 40% ethanol | 15 | 19% | 94% |
| | 30 | 63% | 107% |
| | 45 | 96% | 111% |
| | 60 | 104% | 114% |

While drug release at 5% and 20% alcohol levels were comparable, the formulation of the present disclosure showed significant difference of drug release at 40% ethanol with almost 5 times less drug release at 15 minutes. The drug release of the formulation was further tested after 7 months at 25° C. and 60% Relative Humidity using 0.1N HCl with 40% ethanol. Control testing of the Prevacid® 24 HR capsules was also performed. The results are depicted in Table 8:

TABLE 8

| | | Drug release | |
|---|---|---|---|
| Medium | Time (min) | ODT of the present disclosure | Prevacid ® 24 HR capsules |
| HCl 0.1N + 40% ethanol | 15 | 10% | 84% |
| | 30 | 74% | 121% |
| | 45 | 98% | 125% |
| | 60 | 102% | 122% |

It is noted that after 30 minutes at 0.1N HCl and 40% (v/v) ethanol the drug release of the control Prevacid® 24 HR capsules exceeds 100%. It is believed that these results may stem from the instability of lansoprazole in the tested medium (Ethanolic HCl). Nonetheless, the results are considered indicative for comparison with the composition of the disclosure.

Accordingly, the composition of the present disclosure provides improved resistance to alcohol-induced dose dumping which is maintained even after storage for 7 months.

While certain embodiments of the invention have been illustrated and described, it will be clear that the invention is not limited to the embodiments described herein. Numerous modifications, changes, variations, substitution % and equivalents will be apparent to those skilled in the art without departing from the spirit and scope of the present invention as described by the claims, which follow.

The invention claimed is:

1. An orally disintegrating tablet comprising (i) enteric coated active cores comprising about 2 mg to about 50 mg of a proton pump inhibitor selected from the group consisting of lansoprazole, omeprazole, pantoprazole, leminoprazole, perprazole, rabeprazole, and a pharmaceutically acceptable salt thereof; and (ii) at least one pharmaceutically acceptable excipient comprising a disintegrant comprising cross-linked polyvinylpyrrolidone, the enteric coated active cores comprising:
   (a) inert seeds comprising sugar spheres;
   (b) a drug coating layer over the inert seeds, wherein the drug coating layer comprises the proton pump inhibitor and mannitol, wherein the drug coating layer further comprises at least one alkalizing agent selected from the group consisting of arginine, lysine, meglumine, a stearic acid salt, sodium hydroxide, potassium hydroxide, calcium carbonate, magnesium carbonate, and zinc carbonate, in an amount of about 1% to about 5% by weight of the total composition;
   (c) a subcoating layer over the drug coating layer, wherein the subcoating layer comprises hydroxypropyl methylcellulose; and
   (d) a single enteric coating layer in an amount of about 10% to about 25% by weight of the total composition over the subcoating layer, wherein the enteric coating layer comprises hydroxypropyl methylcellulose phthalate and cetyl alcohol,
   wherein the enteric coated active cores together with the at least one pharmaceutically acceptable excipient comprising a disintegrant are compressed into the form of a tablet,
   wherein the tablet substantially disintegrates in the oral cavity of a subject in need thereof within less than about 60 seconds after administration and provides a delayed release profile of the proton pump inhibitor, and wherein in vitro drug release in 15 minutes at 0.1N HCl and 40% ethanol is less than about 20%.

2. The orally disintegrating tablet of claim 1, wherein the amount of the inert seeds is in the range of from about 2% to about 10% by weight of the total composition.

3. The orally disintegrating tablet of claim 1, wherein the amount of the proton pump inhibitor is in the range of from about 3% to about 9% by weight of the total composition.

4. The orally disintegrating tablet of claim 1, wherein the amount of the subcoating layer is in the range of from about 5% to about 15% by weight of the total composition.

5. The orally disintegrating tablet of claim 1, wherein the proton pump inhibitor comprises 15 mg or 30 mg lansoprazole.

6. The orally disintegrating tablet of claim 1, wherein the amount of the disintegrant is in the range of from about 2% to about 15% by weight of the total composition.

7. The orally disintegrating tablet of claim 1, wherein the proton pump inhibitor comprises lansoprazole.

8. The orally disintegrating tablet of claim 1, wherein the pharmaceutically acceptable excipient further comprises at least one of a binder, a filler, an anti-tacking agent, a lubricant, a glidant, a surfactant, a plasticizer or a combination thereof in an amount of not more than about 30% by weight of the total composition.

9. The orally disintegrating tablet of claim 1, wherein the at least one alkalizing agent comprises meglumine.

10. The orally disintegrating tablet of claim 1, having a hardness of at least 20 Newtons.

11. The orally disintegrating tablet of claim 1, wherein in vitro drug release in 15 minutes at 0.1N HCl and 40% ethanol is less than about 20% after storage for 7 months at 25° C. and 60% Relative Humidity.

12. The orally disintegrating tablet of claim 1, wherein the enteric coating layer over the subcoating layer further comprises triethyl citrate.

13. The orally disintegrating tablet of claim 1, comprising meglumine and lansoprazole in the drug coating layer.

* * * * *